United States Patent [19]
Fedorov et al.

[11] Patent Number: 5,176,139
[45] Date of Patent: Jan. 5, 1993

[54] METHOD FOR ESTIMATION OF INTRAOCULAR PRESSURE USING FREE-FALLING BALL

[76] Inventors: Svyatoslav N. Fedorov, pereulck Dostoevskogo, 1/21, kv. 32, Moscow; Mikhail P. Kozin, prospekt Maslennikova, 19, kv. 15, Samara; Nikolai V. Kudashov, prospekt Lenina, 1, kv. 96, Samara; Jury I. Sakharov, ulitsa Galaktionovskaya, 130, kv. 40, Samara, all of U.S.S.R.

[21] Appl. No.: 722,664

[22] Filed: Jun. 28, 1991

[30] Foreign Application Priority Data

Jun. 26, 1990 [SU] U.S.S.R. .............................. 4846471

[51] Int. Cl.⁵ ................................................ A61B 3/16
[52] U.S. Cl. ........................................ 128/645; 73/79
[58] Field of Search ....................... 128/645, 649, 652; 73/79

[56] References Cited

U.S. PATENT DOCUMENTS 3,038,330 6/1962 Criche ..................................... 73/79
4,336,710 6/1982 Miller ..................................... 73/79

FOREIGN PATENT DOCUMENTS 1187394 3/1962 Fed. Rep. of Germany .......... 73/79

Primary Examiner—Randy C. Shay
Attorney, Agent, or Firm—Burgess, Ryan & Wayne

[57] ABSTRACT

A ball falls freely onto an eyelid-covered cornea, and the kinetic energy of the ball is conversed into a force causing deformation of the cornea. The amount of the ball rebound varies depending on the amount of intraocular pressure and the latter is judged against the amount of the ball rebound.

An ocular tonometer has a tubular housing, wherein provision is made for a free falling of the ball kept by a special holder at one of the ends of the housing. The opposite end of the housing is placed on the eyelid so that the falling ball interacts with the cornea through the eyelid. The amount of the ball rebound characteristic of the amount of intraocular pressure, is registered either with the aid of a scale or by a special measuring instrument.

3 Claims, 4 Drawing Sheets

METHOD FOR ESTIMATION OF INTRAOCULAR PRESSURE USING FREE-FALLING BALL

FIELD OF THE INVENTION

The present invention relates to medicine, more specifically to ophthalmology, and has particular reference to a method for estimation of intraocular pressure and to an ocular tonometer for carrying said method into effect.

The present invention can find application both under clinical conditions as for self-monitoring of the state of intraocular pressure.

BACKGROUND OF THE INVENTION

Intraocular pressure (IOP) is an extremely important characteristic of a physical state of the eye, especially in glaucoma patients and therefore needs periodic, and sometimes permanent monitoring.

The IOP measuring technique most widespread at present is the application of a static pressure to the corneal surface and determination of IOP against its deformation parameters, diameter of the applanation circle, or the depth of deformation for estimation of IOP.

However, such a method requires, on the one hand, preliminary anesthesia application, and on the other hand it provides for a direct contact of the force-transmitting element with the corneal surface, which involves obligatory subsequent sterilization, since the aqueous humor of the eye is in fact an infection transmitter. Use of disposable intermediate elements, however, does not make anesthesia no longer necessary.

Such a method is embodied in a device, comprising a transparent prism, a reference circumference being provided on the prism working surface, having a diameter corresponding to a normal IOP. The device however, suffers from all the disadvantages inherent in the method discussed above.

These disadvantages have been overcome in a device according to French Patent No. 2,542,603, which provides for IOP measurement through the patient's eyelid. Said device comprises a solenoid with a movable armature, said solenoid being enclosed in a casing, a means for preliminary loading of the armature with a preset force, and a sensing element appearing as a piezosensor responsive to armature movement on its interaction with the cornea through the eyelid. Said sensing element is connected to a data processing unit. The device features rather sophisticated construction and its use for self-monitoring is impeded. Moreover, such a device needs periodic readjustment and recalibration, which is due to ageing of the sensing element. And finally, preliminary static loading of the patient's eye envisaged in the patient, renders a substantial influence on the hydrostatic conditions of the eye and introduces non-linear error into the measurement results.

SUMMARY OF THE INVENTION

It is an object of the present invention to provide a method for estimation of intraocular pressure against the amount of a physical force of reaction offered by the cornea deformed through the eyelid.

It is another object of the present invention to provide a simple and reliable device for estimation of the amount of intraocular pressure, which renders self-monitoring of such pressure possible.

One more object of the invention is to simplify the intraocular pressure measuring technique and elimination of disagreeable sensations.

It is a primary and essential object of the invention to provide such a method for estimation of intraocular pressure that takes account of the amount of physical force of reaction offered by a deformed cornea.

The foregoing and further objects are accomplished by a method for estimation of IOP against corneal deformation induced by application of a physical force through the eyelid, according to the invention, used as said physical force is the kinetic energy of a free-falling body, and the amount of the IOP being measured is judged by the amount of the first rebound of said free-falling body.

A disadvantage inherent in the herein-proposed method for IOP estimation resides in its objectiveness, since a dynamic effect produced due to the kinetic energy of a free-falling body, e.g., a ball, remains constant at all times and depends solely on its mass, which is constant for each particular instrument. It must be borne in mind that a dynamic effect due to free-falling body is a transient one and exerts practically no substantial influence upon the state of the hydrodynamic system of the eye. Besides, the amount of a first rebound of the free-falling body is depends practically only of the IOP of the eye under examination, while a correction for elasticity of the eyeball tunics and eyelid may be taken into account during adjustment or calibration of the instrument. And finally, considered as advantageous features of the invention may also be utmost simplicity of technical approach, since the method involves no use of any measuring transducers.

It is expedient that used as a free-falling body is a ball having a mass of from 0.4 to 1.0 g falling from a respective height of 160 and 80 mm. When the ball mass is less than 0.4 g the height must exceed 160 mm, which results, on the one hand, in greater error due to out-of-plumb falling of the ball and hence its rebound, and on the other hand, in a higher eyelid damping effect. Use of a ball having a mass exceeding 1.0 g necessitates a smaller height of ball falling, whereby the height of the ball rebound is also reduced, which affects adversely the estimation accuracy of the measurement results.

The force of the falling ball can be applied either directly to the eyelid or through an intermediate element having a required shape of its tip contacting the eyelid. This makes it possible to select a constant optical shape for interaction with the cornea through the eyelid irrespective of the mass of the ball used and hence of its diameter.

The proposed method can be carried into effect with the aid of an ocular tonometer-indicator, comprising a housing, a reading device, and a force application element, wherein, according to the invention, used as a force application element is a ball enclosed in an oblong casing with a possibility of free falling inside the casing from a holder secured at one end of the casing, towards the opposite end of the casing which is provided with a support for being placed in the patient's eye covered with its lid.

Such an ocular tonometer featuring the function of indication, makes it possible to realize the above-described method in a simplest way, e.g., with the aid of a scale provided with three marks for IOP estimation, said marks dividing the scale into a below-norm, norm, and above-norm zones. The marks are placed with due account of statistical processing of the comparative measurement results.

The ball may be made of any material and must have a mas of from 0.4 to 1.0 g and a length of its falling path within 160 and 80 mm for the reasons stated above.

Inasmuch as the aforesaid ball mass is attained with different ball size, depending on the material the ball is made of, which in turn results in various radii of curvature of the ball surface in contact with the corneal surface, it is expedient that an intermediate force-transmitting element be provided, which has a constant shape and hence constant curvature of the surface that interacts with the corneal surface.

It is also expedient that use be made of a metallic ball, whereby use can be made of a simplest electric sensor of its position upon rebound and of and electric measuring circuit for IOP estimation.

BRIEF DESCRIPTION OF THE DRAWING

In what follows the invention is illustrated in a detailed description of some specific embodiments thereof that place no limitation upon the present invention, and in the accompanying drawings, wherein.

DETAILED DESCRIPTION OF THE PREFERRED EMBODIMENTS

Figure 1:
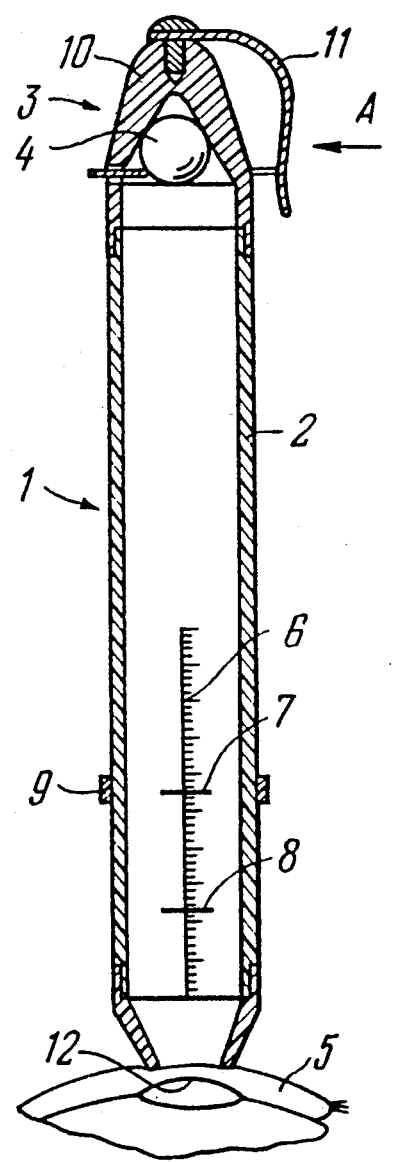
FIG. 1 is a longitudinal sectional view of an embodiment of the tonometer, according to the invention.

Now reference being directed first to FIG. 1, let us consider the mode of function of the proposed tonometer with indication of IOP, from which the essence of the proposed method will likewise become evident.

FIG. 1 illustrates the simplest embodiment of the proposed tonometer. The tonometer, which is indicated as a whole at Reference Numeral 1, is capable of indicating the amount of IOP measured and comprises a transparent tube 2, e.g., a glass one, in whose top portion a holder 3 of a ball 4 is installed in its topmost position, whereas the bottom portion of the tube 2 features a little taper and has a rounded end so as to preclude injury to the tissue of an eyelid 5 when placing the tonometer in position during measurement process. The ball 4 is made of steel. its mass being about 0.7 g, while the length of the housing from the bottom edge interacting with the eyelid 5, to the ball surface is about 120 mm. The diameter of the glass tube must somewhat exceed the diameter of the ball so that with the vertical arrangement of the tube on the eyelid, the ball could perform free falling inside said tube. A scale graduated in mm Hg is provided on the outer surface of the tube 2. Marks 7 and 8 subdivide the scale into three portions that correspond to the amount of IOP below norm, within norm, and above norm, respectively. For user's convenience a movable flag index 9 with a retainer (omitted in the Drawing) is provided on the housing for registering the amount of user's IOP.

The holder 3 of the ball 4 is shaped as a cap 10 located in the top portion of the glass tube 2 and provided with a spring lock 11, which prevents the ball 4 from falling.

The tonometer of the invention is applied as follows.

The instrument is calibrated upon its manufacture, use being made of a special calibrator, for a ball of a known mass. This done, the tonometer is ready for operation.

While in the initial position the ball 4 is inside the cap 10 and is kept in the topmost position by the springs lock 11. Then the patient is asked to close the eyelid, whereupon the tonometer 1 is fitted vertically on a patient's cornea 12 closed by the eyelid 5. The patient's gaze is fixed due to the provision of a flasing light emitter (not shown) situated above the cornea (not shown) of the other (not examined) eye. When under examination the patient can asume either recumbent or sitting position. In the latter case the patient's head should be thrown back in order to fit the tonometer 1 on the eyelid-covered cornea of the patient's eye under examination in a vertical position. One the tonometer 1 has been placed on the eye under examination, one should depress smoothly spring lock 11 (as indicated with an arrow A in FIG. 1). As a result, the ball 4 is released and falls, under the gravitational force, onto the eye-lid covered cornea 12 and, upon interacting with the latter, rebounds. The amount of the first rebound is registerd with the aid of the movable flag index 9 provided with a horizontal mark. The measurements is repeated twice or thrice, the position of the flag index 9 being defined more exactly in the course of the repeated measurements.

Thus, IOP can be measured rather exactly. Measurements taken by the inventors have demonstrated good agreement of the measuring results obtained by using the proposed method with the results of measurements obtained with the aid of some other methods known up till now, e.g., according to Maklakov's technique as can be seen from Table 1, where the results of measurements taken with the use of the proposed tonometer appear as numerator and those of measurements of the same eye taken with the use of a standard Maklakov's tonometer appear as denominator.

TABLE 1

| $\frac{27}{25}$ | $\frac{22}{24}$ | $\frac{20}{21}$ | $\frac{24}{23}$ | $\frac{21}{20}$ | $\frac{21}{19}$ | $\frac{14}{16}$ | $\frac{30}{35}$ | $\frac{15}{14}$ | $\frac{23}{22}$ | $\frac{19}{17}$ | $\frac{11}{13}$ | $\frac{28}{31}$ | $\frac{36}{41}$ |
|---|---|---|---|---|---|---|---|---|---|---|---|---|---|
| $\frac{21}{18}$ | $\frac{20}{22}$ | $\frac{19}{17}$ | $\frac{30}{36}$ | $\frac{31}{38}$ | $\frac{17}{18}$ | $\frac{21}{19}$ | $\frac{23}{21}$ | $\frac{24}{26}$ | $\frac{19}{17}$ | $\frac{18}{19}$ | $\frac{20}{21}$ | $\frac{17}{15}$ | $\frac{21}{18}$ |
| $\frac{18}{20}$ | $\frac{20}{19}$ | $\frac{35}{43}$ | $\frac{11}{12}$ | $\frac{13}{15}$ | $\frac{27}{31}$ | | | | | | | | |

Whenever the useer is interested only in estimation of his/her IOP, that is, in determining whether it is within the normal limits but is not interested in obtaining its exact amount, it is attainable by using the marks 7 and 8 made on the glass tube to define the upper and lower boundaries of permissible IOP values.

The aforestated physical parameters, that is, the ball mass within a range of 0.4 and 1.0 g and the glass tube length within 160 and 80 mm have been selected experimentally and ensure adequately good test results.

Figure 2:
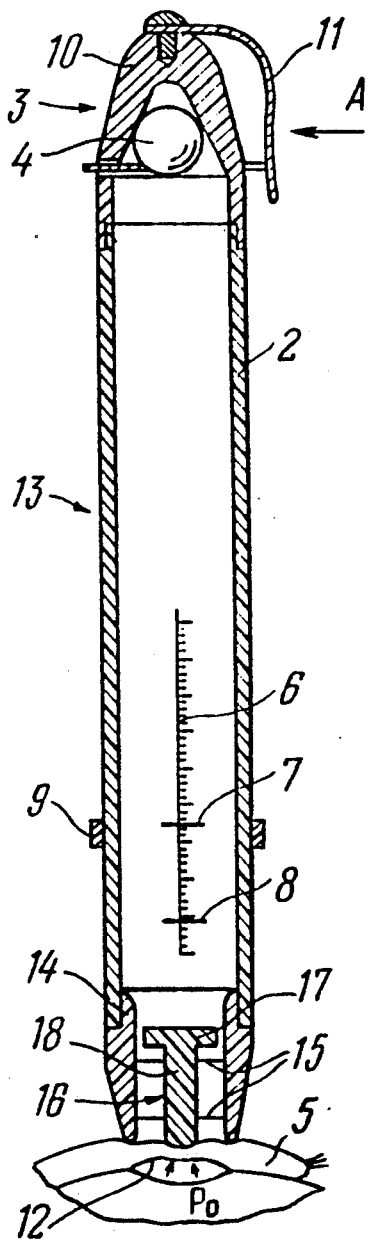
FIG. 2 illustrates the proposed tonometer with a force-transmitting element.

We have conducted a number of experiments with the use of balls made of various materials and having therefore different diameters, the results of such experiments being rather satisfactory. It should however be noticed that the larger the ball diameter the lower the IOP measurement results. Therefore in order to retain the measurement accuracy invariably exact irrespective of the ball size, use can be made of a tonometer-indicator as shown in FIG. 2, wherein like reference numerals denote the components similar to those shown in FIG. 1. The sole difference of the tonometer-indicator 13 shown in FIG. 2 resides in that it has a supporting sleeve 14 located in the tonometer bottom portion and carrying a force-transmitting element 16, which is fixed in place through leaf springs 15 and has a T-shaped cross-section. A top component of the element 16 is in the form of a flat disk 17, while an element 18 square with the disk 17 is in effect a rounded-end cylinder. In such a construction the area of a force application to the corneal surface is featured by a constant radius of curvature. Besides, the springs 15 provide for preliminary deformation of the patient's eyelid. The aforementioned factors contribute to higher accuracy of IOP estimation.

The mode of use and of functioning of the tomometer shown in FIG. 2 are similar to those of the tonometer shown in FIG. 1 with the sole exception that the ball 4 falls upon the flat disk 17 of the force-transmitting element 16 and acts upon the eyelid-covered corneal surface through said T-shaped element.

It is evident from all stated hereinbefore that the gist of the proposed method for IOP measurement resides in conversion of the kinetic energy of a free-falling body into a physical force applied to the cornea through the eyelid, thus causing the corneal surface to deflect. The magnitude of the corneal reaction force and hence the amount of the first rebound of the fallen body is the function of the value $P_o$ of IOP. In this case the effect of the eyelid is negligibly small and therefore tells on the results of IOP measurement but insignificantly.

The tonometer shown in FIGS. 1 and 2 is capable of patient's IOP measurement performed by any person, even by those having no special training, since the only taks to be carried out is to determine the topmost position of the ball after its first rebound. However, this offers some inconvenience and fails to provide a possibility of self-monitoring.

Figure 3:
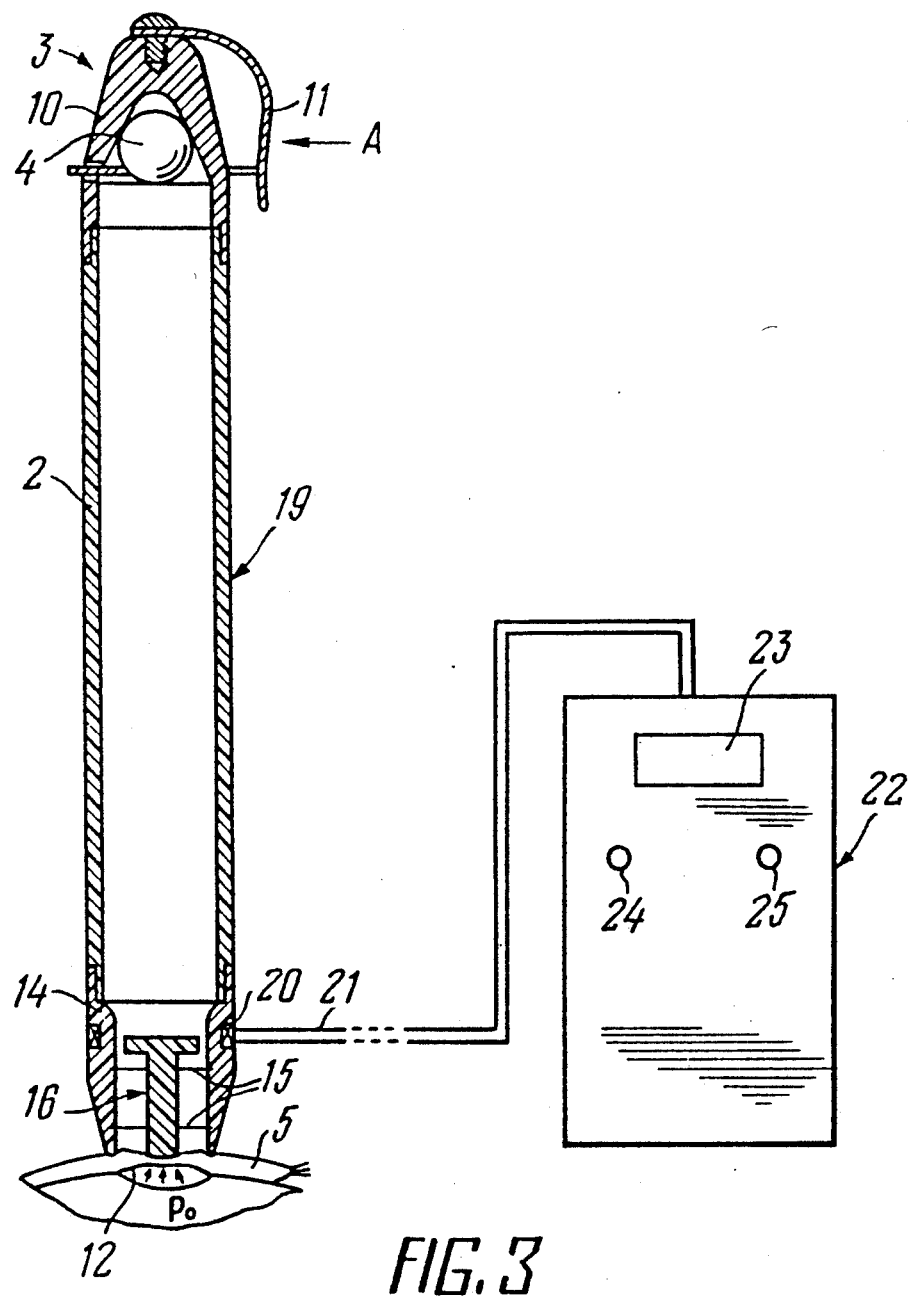
FIG. 3 shows the proposed tonometer with an electrical sensor of the position of a ball for IOP indication.

The tonometer shown in FIG. 3 allows electronic processing of the measurement results to obtain them in a readily intelligible form, e.g., in the digital form, as well as of storing the measurement results, which makes possible self-monitoring of IOP.

The components of the tonometer shown in FIG. 3 similar to those of the tonometer shown in FIG. 2, are indicated with the like Ref. Nos.

The tonometer indicated as a whole by Ref. No. 19 in FIG. 3, comprises additionally an inductor coil 20 situated in the sleeve 14 in the vicinity of the flat disk 17 of the force-transmitting element 16. The coil 20 is electrically connected, through connecting wires 21, to an electronic metering unit 22 having an indicator 23, e.g., a digital one, which presents the value of the IOP meausred in mm Hg, said value being retained and can be reset upon depressing a reset button 24. Individual tonometer adjustment for a particular patient in case of personal use of the instrument is carried out with the aid of a calibrator 25. In this case first the amount of the patient's IOP is measured with the aid of a reference instrument, then a corresponding IOP value is set, by the knob of the calibrator 25, upon taking measurement with the aid of the tonometer shown in FIG. 3.

As a matter of fact, the metering unit of the tonometer shown in FIG. 3 is for determining the height of the first rebound of the ball 4 proceeding from the result of measurement of a time lapse between the first and second interactions of the ball 4 with the force-transmitting element. Indeed, when the ball rises after rebound for a difinite height h and them falls again onto the force-transmitting element 16, the height of the first ball rebound can readily be found by the commonly known formula $$h = \frac{gt^2}{2},$$

if one has knowledge of the time t.

In the simplest cassae the metering unit 22 may be implemented with the aid of a time-delay relay (omitted in the Drawing) and a converter (also omitted in the Drawing) of the timer output signal into the linear units of the ball rebound height, since time and height are definitively interrelated through the aforementioned relationship. In this case the relay is energized in response to a first signal arrived from the inductor coil 20 to start counting off time, while in response to a second signal delivered by the coil 20 and generated upon a second interaction of the ball with the force-transmitting element, that is, after ball rebound and falling again, the relay gets deenergized, and its signal is converted into the amount of height of the ball rebound and is displayed by the indicator 23 shaped as a scale graduated in the IOP units.

Figure 4:
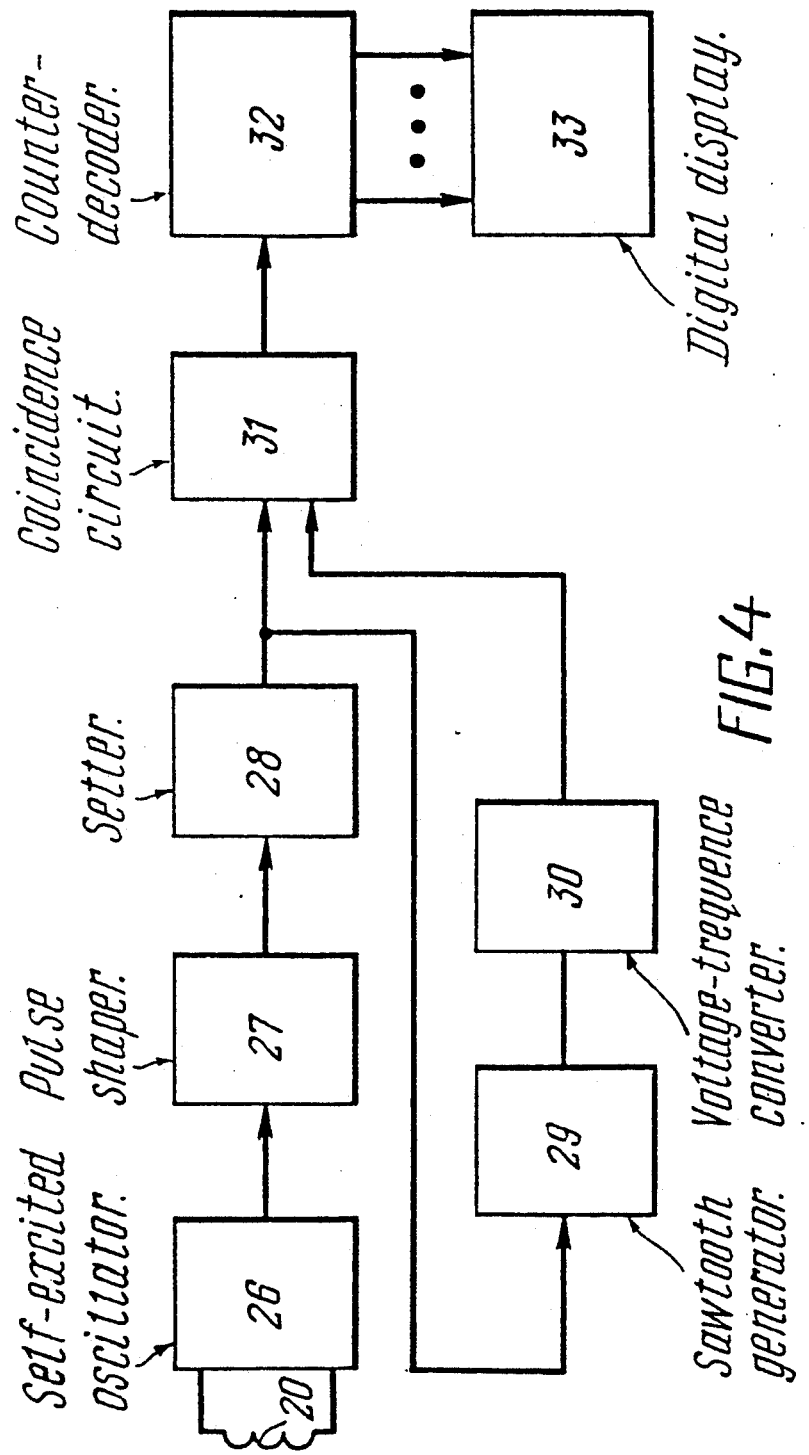
FIG. 4 is a block-diagram of the measuring unit of the tonometer, according to the invention.
Figure 5:
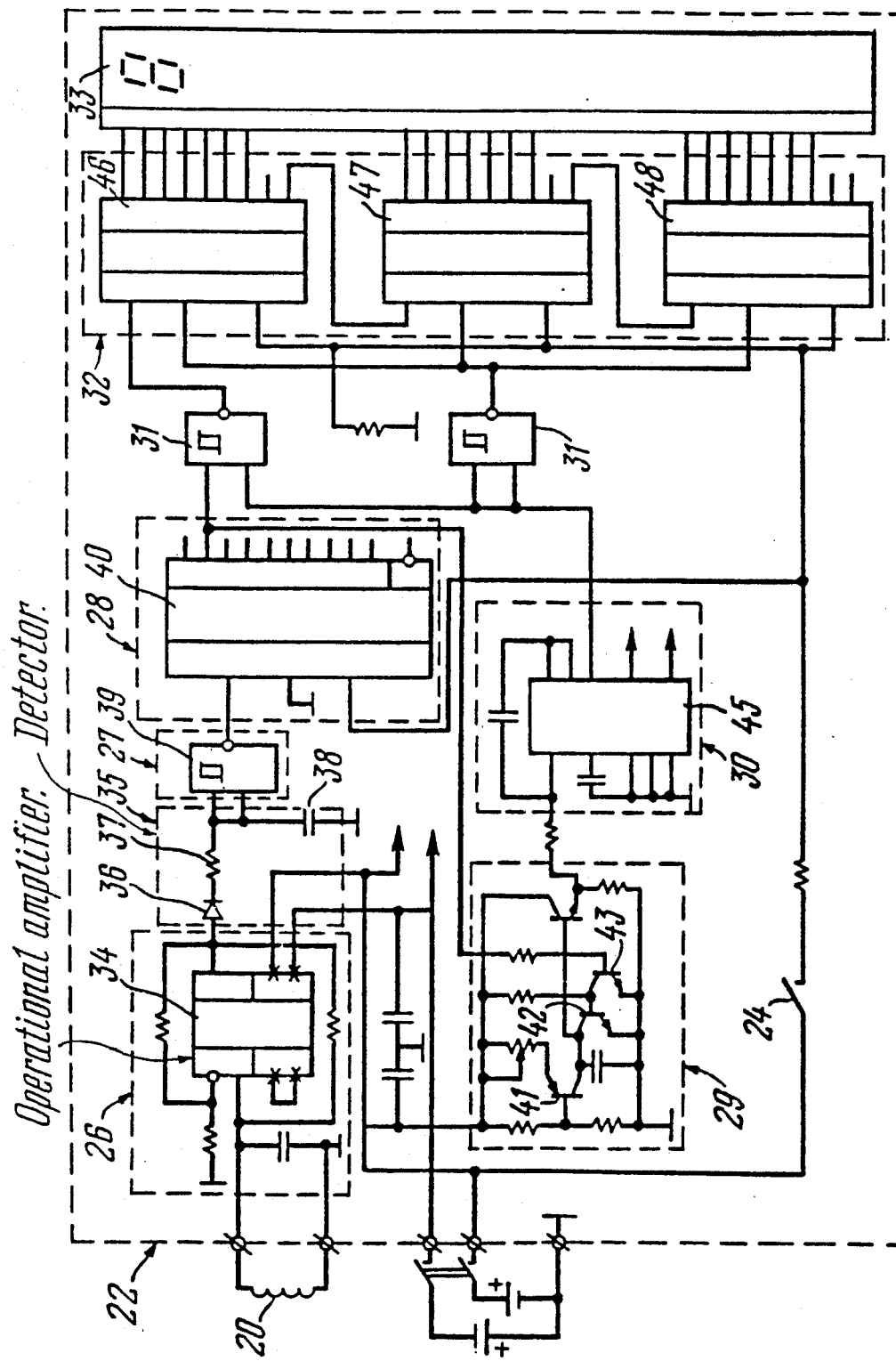
FIG. 5 is an elementary diagram of the measuring unit of the tonometer, according to the invention.

Higher precision of measurements is attainable upon making use of an electronic unit specially adapted for the purpose and shown in FIGS. 4 and 5.

A functional block-diagram of the electronic metering unit 22 as shown in FIG. 4, comprises a self-excited oscillator 26, whose circuit incorporates the coil 20 (FIG. 3), a shaper 27 of electric pulses, measuring time interval setter 28, a sawtooth generator 29, a voltage-frequency converter 30, a coincidence circuit 31, a counter-decoder 32, and a digital display 33.

The afore-described block-diagram for measuring a time interval between the first and second fallings of the ball onto the disk 17 of the force-transmitting element 16 and determining the height of rebound against time.

With the ball 4 assuming its topmost initial position, i.e., when the ball is kept in that position with the aid of the holder 3 (FIG. 3), the self-excited oscillator 26 is enabled to generate a voltage appearing at its output and applied to the input of the pulse shaper 27 at whose output a zero level signal is present. Upon free falling of the ball 4 it gets in the field of the coil 20 (FIG. 3) at the instant of its action upon the force-transmitting element 16. This causes queching of the ocillations produced by the self-excited oscillator 26 due to a reduced Q-factor of the coil 20. Quenching of the oscillators generated by the self-excited oscillator 26 results in turn in a zero voltage at the input of the pulse shaper 27, whereas the output voltage of the pulse shaper 27 changes suddenly from the zero to the unity level, that is, a type 0→1 transition occurs at the output of the pulse shaper 27 in case of quenched oscillations generated by the self-excited oscillator 26. Such a change of state, after having been impressed upon the input of the setter 28, causes its state to change, too, which corresponds to the start of a measuring time interval. Interaction of the force-transmitting element 16 and per FIG. 3 with the cornea of the eyelid-covered eye causes the ball 4 to rebound. As a result, the influence produced by the ball 4 on the inductance value of the coil 20 (FIG. 3), which causes the oscillator 26 to resume generation of oscillations and increases the voltage applied to the input of the pulse shaper 27, while its output voltage drops to zero. While rebounding the ball 4 reaches a certain height h above the flat disk 17 of the force-transmitting element 16 and then falls freely onto the said element (FIG. 3). It is at the instant of interaction of the ball 4 with the element 16 that the oscillations produced by the self-excited oscillator 26 are quenched, which reduces the input voltage of the pulse shaper 27 and causes the appearance of a type 0→1 transition at the output of the pulse-shaper 27, said transition changing the state of the setter 28. Such a change indicates the end of the time interval being measured. Thus, a measuring time interval is shaped at the output of the setter 28, which is proportional to the time of rebound of the ball 4. As it has been stated above, the height h of rebound of the ball 4 is characteristic of the amount of IOP in the eye under examination. Said height is related to the rebound time, i.e., to the duration of the measuring time interval t, through the following relationship:

$$h = \frac{gt^2}{2},$$

where g is gravitational acceleration.

It ensures from the relationship stated above that the result presented in the display of the proposed tonometer should be directly proportional to the square of the time interval t as shaped at the output of the pulse shaper 28. To this aim, a signal from the output of the setter 28 is supplied to the input of the sawtooth generator 29, and its linearly-rising output voltage is applied to the voltage-frequency converter 30. Then a pulsed output voltage is fed from the output of the converter 30 to one of the inputs of the coincidence circuit 31, while delivered to the second input thereof is the output signal from the setter 28, whose duration corresponds to the time of the first rebound of the ball 4. Thus, the number f of pulse will arrive at the input of the counter-decoder 32 for the time interval t, said number being dependent on the relationship:

$$r = kt^2,$$

where k is the proportionality factor that depends on the coefficients of conversion of the sawtooth generator 29 and of the voltage-frequency converter 30.

The values of the coefficient of conversion of the generator 29 and of the converter 30 are so selected that measurement result obtained in the digital display 33 should correspond to the amount of true IOP in the eye under examination. To this end, the knob of the calibrator 25 is brought to the front panel of the metering unit 22 as control member with the aid of which the coefficient of conversion of e.g., the generator 29 can be changed.

Individual adjustment of the tonometer-indicator shown in FIG. 3 for a particular patient, using the diagram of FIG. 4 is carried out as follows. The true IOP value $P_o$ of a patient is measured by a reference tonometer under conditions of e.g., a clinic. With the patient assuming the same positon, his/her IOP is measured with the aid of the tonometer-indicator shown in FIG. 3 and, using the knob of the calibrator 25, one seeks for the same reading in its digital display that has been obtained with the aid of the reference tonometer. Afterwards the patient can be make use of the tonometer indicator under domestic conditions for monitoring the amount of his/her IOP, taking care not to upset the position of the knob of the calibrator 25.

FIG. 5 illustrates a version of an elementary electric diagram that corresponds to the functional block-diagram of FIG. 4. Herein the self-excited oscillator 26 of the block-diagram of FIG. 4 is built around an operational amplifier 34 according a classical arrangement. The circuit of the oscillator 26 incorporates the coil 20 as per FIG. 3. A detector 35 is connected to the output of the self-excited oscillator 26, which is made up of a diode 36, a resistor 37, and a capacitor 38. The output resistance from the detector is applied to the input of the pulse shaper 27, which is built around a Schmitt flip-flop 39 as shown in the diagram of FIG. 5. The measuring time measuring setter 28 is implemented with the aid of a Johnson counter 40 as shown in the diagram of FIG. 5. The sawtooth generator 29 of FIG. 4 is built around of a number of transistors as shown in the diagram of FIG. 5, wherein a transistor 41 functions as a current generator, transistors 42 and 43 define a switch, while a transistor 44 is in effect an emitter follower. A linearly increasing voltage is fed from the output of the generator 29 to the input of the voltage-frequency converter 30 of FIG. 4, which is implemented with the aid of a standard voltage-controlled generator 45 as shown in the diagram of FIG. 5. The coincidence circuit 31 of FIG. 4 is built around a circuit performing the logic NAND function. The output signal of the coincidence circuit is fed to the input of the counter-decoder 32 of FIG. 4, which is built around three series-connected binary-decimal counters-decoders 46, 47, 48 as shown in the diagram of FIG. 5. The output lines of the counters-decoders are connected to the respective leads of the segments of the digital display 33, which presents the IOP measurement results. Using the button 24 (FIG. 3) one carries out reset of the preceding measurement results and preparation of the tonemeter for a next measurement. Power is drawn by the circuitry from supply batteries B1, B2 controlled by a switch 49.

The principle of operation of the aforedescribed measuring circuit is left beyond the present Specification, since it is quite evident for those skilled in the art and is therefore set forth in the present description for the sake of illustration only.

Though the present invention is described in connection with the preferred embodiments thereof, it should be understood, however, that various changes and modifications may be made without departing from the spirit and scope of the present invention. Thus, for instance, use may be made of another measuring circuit for determining the amount of the first ball rebound. The housing of the instruments may be provided with a special support for its being installed in a vertical position, and the ball holder may have an alternative construction.

Industrial Applicability

The proposed ocular tonometer can find widespread application both clinically and personal use.

What we claim is:

1. A method for estimation of intraocular pressure, comprising:
   covering the cornea with the eyelid;
   effecting free falling of a ball upon the eyelid-covered cornea, with the result that the kinetic energy of said ball is converted into a force that causes corneal deformation and a rebound of the ball upward from the cornea, and
   determining the height of the ball, upon said rebound after said free falling thereof, and interpreting the amount of intraocular pressure from the height of the rebound.

2. A method as claimed in claim 1, wherein the ball has a mess of from about 0.4 to about 1.0 g and free falls from a height of from about 160 to about 80 mm, respectively.

3. A method as claimed in claim 2, wherein kinetic energy is converted into a force applied, through the eyelid, to the cornea, by virtue of an intermediate element.

* * * * *